(12) United States Patent
Otto

(10) Patent No.: US 8,119,376 B2
(45) Date of Patent: Feb. 21, 2012

(54) METHOD FOR THE PRODUCTION OF LACTIC ACID OR A SALT THEREOF BY SIMULTANEOUS SACCHARIFICATION AND FERMENTATION OF STARCH

(75) Inventor: Roel Otto, Gorinchem (NL)

(73) Assignee: Purac Biochem B.V., Gorinchem (NL)

( * ) Notice: Subject to any disclaimer, the term of this patent is extended or adjusted under 35 U.S.C. 154(b) by 976 days.

(21) Appl. No.: 10/514,161

(22) PCT Filed: May 13, 2003

(86) PCT No.: PCT/EP03/50159
§ 371 (c)(1),
(2), (4) Date: Dec. 21, 2004

(87) PCT Pub. No.: WO03/095659
PCT Pub. Date: Nov. 20, 2003

(65) Prior Publication Data
US 2005/0176120 A1 Aug. 11, 2005

(30) Foreign Application Priority Data
May 14, 2002 (EP) .................................... 02076954
Jun. 10, 2002 (EP) .................................... 02077648

(51) Int. Cl.
C12P 7/56 (2006.01)
C12P 7/40 (2006.01)
C12P 7/00 (2006.01)
C12P 1/00 (2006.01)
C12N 1/12 (2006.01)

(52) U.S. Cl. .......... 435/139; 435/41; 435/132; 435/136; 435/252.1

(58) Field of Classification Search .................... 435/139
See application file for complete search history.

(56) References Cited

U.S. PATENT DOCUMENTS

| 5,079,164 A | 1/1992 | Kirkovits et al. |
| 5,464,760 A | 11/1995 | Tsai et al. |
| 6,022,537 A | 2/2000 | Combet-Blanc et al. |

FOREIGN PATENT DOCUMENTS

| DE | 40 00 942 A1 | 9/1990 |
| EP | 0 346 983 | 12/1989 |
| EP | 0 354 828 | 2/1990 |
| WO | WO 02/074934 A1 * | 9/2002 |

OTHER PUBLICATIONS

Schneider, et al. "Method of Producing Lactic Acid." 1990. [USPTO Translation of EP0354828. Prepared Feb. 2006.].*
Nakamura et al., "Taxonomic Study of *Bacillus coagulans* Hammer 1915 with a Proposal for *Bacillus smithii* sp. nov.," International Journal of Systematic Bacteriology, No. 1, pp. 63-73 {Jan. 1988}.
Hofvendahl et al, "Simultaneous Enzymatic Wheat Starch Saccharification and Fermentation to Lactic Acid by *Lactococcus lactis*," Appl Microbiol Biotechnol: vol. 52, pp. 163-169 {Feb. 20, 1999}.
Linko et al, "Simultaneous Liquefaction, Saccharification, and Lactic Acid Fermentation on Barley Starch," Enzyme and Microbial Technology, vol. 19, pp. 118-123 {Aug. 19961}.
Mercier et al., "Kinetics of Lactic Acid Fermentation on Glucose and Corn by *Lactobacillus amylophilus*," J. Chem. Tech. Biotechnol, vol. 55, pp. 111-121 {1992}.
Cheng et al., "Lactic Acid Production from Enzyme-Thinned Corn Starch Using *Lactobacillus amylovorus*," Journal of Industrial Microbiology, No. 7, pp. 27-34 {1991}.
Zhang et al., "Direct Fermentation of Starch to Lactic Acid by *Lactobacillus amylovorus*," Biotechnology Letters, vol. 13, No. 10, pp. 733-738 {1991}.
Tsai et al., "An Integrated Bioconversion Process for Production of $_L$ - Lactic Acid from Starchy Potato Feedstocks," Applied Biochemistry and Biotechnology, vol. 70-72, pp. 417-428 {1998}.
Olsen, "Kernisk," vol. 25, No. 7, pp. 125-130 {1944} with translation.
Payot et al., "Lactic Acid Production by *Bacillus coagulans*—Kinetic Studies and Optimization of Culture Medium for Batch and Continuous Fermentations," Enzyme and Microbial Technology, vol. 24, pp. 191-199 {1999}.
Combet-Blanc et al., "Effect of Organic Complex Compounds on *Bacillus thermoamylovorans* Growth and Glucose Fermentation," Applied and Environmental Microbiology, vol. 65, No. 10, pp. 4582-4585 {Oct. 1999}.
Combet-Blanc et al., "Effect of pH on *Bacillus termoamylovorans* Growth and Glucose Fermentation," Applied and Environmental Microbiology, vol. 61, No. 2 , pp. 656-659 {Feb. 1995}.
Combet-Blanc et al., "*Bacillus thermoamylovorans* sp. Nov., a Moderately Thermophilic and Amylolytic Bacterium," International Journal of Systematic Bacteriology, vol. 45, No. 1, p. 9-16 {Jan. 1995}.
Pearsall. *The New Oxford Dictionary of English*, 1998, p. 19.
Coombs. *Macmillan Dictionary of Biotechnology*, $2^{nd}$ edition, 1992, p. 337.
James et al. "Purification of Glucoamylase from *Lactobacillus amylovorus* ATCC 33261," Current Microbiology 34, 1997, p. 186-191.
Hanson et al. "Kinetic Studies of the Lactic Acid Fermentation in Batch and Continuous Cultures," Biotechnology and Bioengineering 14, 1972, p. 232-252.
Giraud et al. "Degradation of Raw Starch by a Wild Amylolytic Strain of *Lactobacillus plantarum*," Applied and Environmental Microbiology, 1994, p. 4319-4323.

(Continued)

Primary Examiner — Ruth Davis
Assistant Examiner — Sheridan MacAuley
(74) Attorney, Agent, or Firm — Oliff & Berridge, PLC

(57) ABSTRACT

The present invention pertains to a method for the production of lactic acid or a salt thereof wherein starch is subjected to a process of simultaneous saccharification and fermentation, the method comprising saccharifying starch in a medium comprising at least a glucoamylase and simultaneously fermenting the starch using a microorganism, and optionally isolating lactic acid from the medium, characterized in that a moderately thermophilic lactic acid-producing microorganism is used. The invention further relates to a method of performing said process in the presence of a moderately thermophilic lactic acid producing microorganism, which has been adapted to have its maximum performance at the working pH.

12 Claims, No Drawings

OTHER PUBLICATIONS

Chaplin. "The use of enzymes in starch hydrolysis," http://www.lsbu.ac.uk/biology/enztech/starch.html, London South Bank University, 2004, accessed Oct. 3, 2008.

Demirci et al. Enhanced production of D(−)-lactic acid by mutants of *Lactobacillus delbruekii* ATCC 9649, *Journal of Industrial Microbiology*, 11 (1992), p. 23-28.

Singleton et al. *Dictionary of Microbiology and Molecular Biology*, 2nd edition, 1987, p. 13, 533 and 882.

H. Danner et al., "*Bacillus stearothermophilus* for Thermophilic Production of L-Lactic Acid", Appl. Biochem. Biotechnol.—Part A Enzyme Engineering and Biotechnology, vol. 70-72 (1998), pp. 895-903.

I. Andersch et al., "Description of *Bacillus laevolacticus* (ex Nakayama and Yanoshi 1967) sp. nov., nom. rev." International Journal of Systematic Bacteriology, vol. 44, No. 4 (1994), pp. 659-664.

Feb. 8, 2011 Office Action issued in U. S. Appl. No. 12/155,180.

Office Action, U.S. Appl. No. 12/155,177, dated Nov. 25, 2009.

Office Action, U.S. Appl. No. 12/155,180, dated Nov. 25, 2009.

Dec. 8, 2011 Office Action issued in U.S. Appl. No. 12/155,180.

\* cited by examiner

METHOD FOR THE PRODUCTION OF LACTIC ACID OR A SALT THEREOF BY SIMULTANEOUS SACCHARIFICATION AND FERMENTATION OF STARCH

The present invention pertains to a method for the production of lactic acid or a salt thereof wherein starch is subjected to a process of simultaneous saccharification and fermentation.

Fermentation processes are exploited for the manufacture of a vast number of products of considerable commercial interest and which are difficult to produce synthetically. Fermentation is used in industry to produce simple compounds among which alcohols, such as ethanol and butanol; organic acids, such as citric acid, itaconic acid, (R)- or (S)-lactic acid and gluconic acid; ketones; amino acids, such as glutamic acid and lysine; but also more complex compounds as antibiotics, such as penicillin and tetracyclin; enzymes; vitamins, such as riboflavin, vitamin B12 and beta-carotene; and hormones. Also in the brewing, wine, dairy, leather and tobacco industry fermentation processes are used.

Sugar is the most important contributor to the manufacturing cost price of lactic acid. Major reductions in the manufacturing cost price of lactic acid can therefore be accomplished if the manufacturing process is fed with cheap sugar. Starch and partial hydrolysates of starch, the latter also known as liquefied starch, which can also be purified to products such as maltooligosaccharides or maltodextrines, represent such cheap sources. The term "liquefied starch" means starch that has been subjected to the process of liquefaction, which means acid, enzymic, or thermomechanical fluidification of starch leading to a dissolved or soluble form. The term "malto-oligosaccharides" means maltosaccharides composed of α-1,4-glucosidic linkages of anhydroglucose units having a degree of polymerization ($DP_n$) of 2-50 (n) such as maltose, maltotriose, maltotetraose, or maltopentaose and the like. The term "degree of polymerization" or $DP_n$ means the number of anhydroglucopyranose units in a given saccharide. Maltose, having two α-1,4-glucosidic linked glucose residues may be referred to as $DP_2$; maltotriose, having three α-1,4-glucosidic linked glucose residues may be referred to as $DP_3$ and so on. The term "maltodextrin" means a starch hydrolysis product having a DE of less than 20. The term "DE" (dextrose equivalent) means the reducing power (loss of electrons due to presence of carbonyl function) expressed as D-glucose on a dry basis. The term "dry basis" means the composition based on the absence of water. For instance, a product containing 25 wt. % of component A, 25 wt. % of component B and 50 wt. % of water would contain 50 wt. % of component A (or B) on a dry basis. The term "lactic acid" means 2-hydroxy-propionic acid in either its free acid or salt form. The salt form of lactate is specifically referred to as lactate-salt, e.g. as either the calcium salt of lactic acid or calcium lactate. Alkali and earth alkali metal salts of lactic acid are preferred. Lactic acid contains a chiral carbon atom, and for that reason can exist as (R) and (S) enantiomer. The term "lactic acid" as used in this application includes the pure (R) and (S) isomers, and mixtures thereof including the racemic mixture. The term "enantiomeric purity" for an excess (S)-isomer means Enantiomeric purity=100%×{((S)-isomer)/((R)-isomer+(S)-isomer)}

The term "enantiomeric purity" for an excess (R)-isomer means

Enantiomeric purity=100%×{((R)-isomer)/((R)-isomer+(S)-isomer)}

Many microorganisms, which are used for fermentation processes are unable to ferment starch, liquefied starch, malto-dextrines or maltooligosaccharides since they lack either the enzymic machinery to liquefy starch or the enzymic machinery for saccharification or they lack both. The term "saccharification" means the acid- or enzymic-hydrolysis of starch or liquefied starch or maltodextrines or maltooligosaccharides that ultimately results in the production of D-glucose or maltose or small maltooligosaccharides or mixtures thereof. Fortifying cultures of these microorganisms with preparations of α-amylases or glucoamylases or pullulanase or mixtures thereof can conveniently solve this incompatibility problem. The term "α-amylase" means an enzyme belonging to the functional-class with the EC number 3.2.1.1 and the trivial name glycogenase, diastase, fungal α-amylase, or bacterial α-amylase, and the systematic name 1,4-α-D-glucan glucanohydrolase. α-Amylases partially depolymerize polysaccharides containing three or more 1,4-α-linked D-glucose units by endohydrolysis of 1,4-α-D-glucosidic linkages. The term "glucoamylase" means an enzyme belonging to the functional-class with the EC number 3.2.1.3 and the trivial name glucoamylase, γ-amylase, lysosomal α-glucosidase, acid maltase, exo-1,4-α-glucosidase, glucozyme, AMG, or GAM, and the systematic name 1,4-α-D-glucan glucohydrolase. Glucoamylases hydrolyze terminal 1,4-linked α-D-glucose residues successively from the non-reducing ends of the chains with release of β-D-glucose, and they hydrolyze the α-1,6 linkages. The term "pullulanase" means an enzyme belonging to the functional-class with the EC number 3.2.1.41 and the trivial name limit-dextrinase, debranching enzyme, or amylopectin 6-glucanohydrolase, and the systematic name α-dextrin-6-glucanohydrolase or pullulan 6-glucanohydrolase. Pullulanases debranched starch by hydrolysing the α-1,6 linkages. The term "starch" means any purified or crude starch or liquefied starch, or any starch- or liquefied starch-containing material. Wheat, corn, rye, and potato starch are examples of starches that can usefully be applied in the present invention.

Systems that combine the saccharification of starch or liquefied starch and fermentation of the saccharification products (glucose, maltose, small malto-oligosaccharides) are known as "simultaneous saccharification and fermentation" (SSF) processes. SSF systems hold considerable promise.

Fermentation of starch or liquefied starch to lactic acid is known in the art, for example from EP 354828 A1, wherein a process for producing lactic acid is disclosed, which includes incubating *Lactobacillus delbrueckii* subsp *lactis* or *Lactobacillus rhamnosus* in fermentation broth containing liquefied wheat starch and a preparation of a glucoamylase to produce a lactate-containing fermentation broth. Hofvendahl et al in *Appl. Biochem. Biotechnol.*, 52: 163-169 (1999) describe an SSF-system with *Lactococcus lactis* in fermentation broth-containing wheat starch. Linko et al in *Enz. Microb. Technol.*, 19: 118-123 (1996) describe an SSF-system with *Lactobacillus casei* in fermentation broth-containing barley starch. U.S. Pat. No. 2,588,460 discloses a process to produce lactic acid which includes incubating *Lactobacillus delbrueckii* in fermentation broth-containing liquefied corn starch and a preparation of a glucoamylase to produce a lactate-containing fermentation broth. Mercier et al in *J. Chem. Technol. Biotechnol.*, 55: 111-121 (1992) describe an SSF-system with *Lactobacillus amylophilus* in fermentation broth-containing liquefied corn starch. Cheng et al in *J. Indust. Microbiol.*, 7: 27-34 (1991) and Zhang et al in *Biotechnol. Letters*, 13: 733-738 (1991) describe an SSF-system with *Lactobacillus amylovorus* in fermentation broth-containing liquefied corn starch. In U.S. Pat. No. 5,464,760 and WO 94/13826 processes to produce lactic acid are disclosed, which include incubating a mixed culture of (R)- and (S)-lactic acid-producing *Lactobacillus* species in fermentation broth-containing liquefied potato starch and a preparation of a glucoamylase to produce a lactate-containing fermentation broth. Tsai et al in *Appl. Biochem. Biotechnol.*, 70/72: 417-428 (1998) describe an SSF-system with a *Lactobacillus* species in fermentation broth-containing potato starch. The term "fermentation broth" refers to both media in the form originally provided to microorganisms as a source of nutrients, growth factors and carbohydrates and media produced after some or all of the originally provided nutrients, growth factors, or carbohydrates have been consumed and fermentation products including lactic acid have been excreted into the media by the microorganisms.

Although microorganisms such as *Lactobacillus* species, *Lactococcus* species, *Streptococcus* species, *Enterococcus* species, and *Sporolactobacillus* species are producers of lactic acid, certain properties make these organisms less suitable for the industrial manufacture of lactic acid, including the fact that they have a growth temperature in the range of 30-50° C., with an optimum at 30-37° C., which makes it more difficult to avoid infections in industrial scale fermentation systems, which compromise the enantiomeric purity of the lactic acid during the fermentation than when higher temperatures can be used.

It is one of the objects of this invention to provide a method, which is devoid of this disadvantage of the known SSF processes.

Furthermore the growth-temperature range of these microorganisms is not congruent with the application temperature range of glucoamylase and pullulanase, which is in the range of 50-70° C. and of α-amylase, which is in the range 80-105° C. A lactic fermentation with the microorganisms operated as SSF at a temperature which is optimal for these microorganism is sub-optimal for the activity of the enzyme. These reduced activities can be compensated by adding more glucoamylase, pullulanase or α-amylase or mixtures thereof, but this will add to the costs. Furthermore, these organisms require a fair amount of organic nitrogen in the fermentation medium, as well as growth promoting substances, so that the broth becomes more expensive and the lactic acid becomes more difficult to purify than when a simple fermentation medium can be used. On the part of these considerations it was found that more thermophilic nutritionally less demanding lactic acid-producing bacteria are more favorable.

The invention therefore pertains to a method for the production of lactic acid or a salt thereof wherein starch is subjected to a process of simultaneous saccharification and fermentation, the method comprising saccharifying starch in a medium comprising at least a glucoamylase and simultaneously fermenting the starch using a microorganism, and optionally isolating lactic acid from the medium, characterized in that a moderately thermophilic lactic acid-producing microorganism is used.

The use of moderately thermophilic *Bacillus* species for the manufacture of lactic acid from simple sugars such as glucose and sucrose is known in the art. The term "moderately thermophilic" means bacterial strains, which are capable of growing at temperatures between 30-65° C., with an optimum between 40-60° C., more preferably between 50-60° C. U.S. Pat. No. 5,002,881 and DE 4000942 disclose processes to produce lactic acid which include incubating strains of *Bacillus coagulans* at 48-54° C. in a simple fermentation medium containing either glucose or sucrose as carbohydrate to produce a lactate containing fermentation broth. DE 4000942, Olsen in *Kemisk*, 25: 125-130 (1944) and Payot et al in *Enzyme Microb. Technol.*, 24: 191-199 (1999) describe a lactic fermentation at 50-60° C. without sterile conditions with *Bacillus coagulans* (i.e. *Lactobacillus cereale*) in fermentation medium with sucrose as carbohydrate to produce a lactate-containing broth. U.S. Pat. No. 6,022,537 discloses a moderately thermophilic amylolytic organism, *Bacillus thermoamylovorans*, which is useful for producing lactic acid.

The use of moderately thermophilic lactic acid producing strains for the manufacture of lactic acid from starch (or liquefied starch) with SSF technology, however, has never been disclosed and has now been found to advantageously solve the temperature non-congruency that exists between the microorganism and the glucoamylase or pullulanase and to improve it for α-amylase. It is a further advantage of the present invention that enantiomerically pure lactic acid or a salt thereof can now easily be prepared. The term "enantiomerically pure" means that the enantiomeric purity is at least 95%, preferably at least 98%, and more preferably at least 99%. Although *Bacillus coagulans* and *Bacillus thermoamylovorans* are excellent lactate producers, they also have certain properties which at first sight would render these organisms less suitable candidates for the manufacture of enantiomerically pure lactic acid from starch or liquefied starch. *Bacillus thermoamylovorans* is heterolactic, which means that a fraction of the carbohydrate substrate is fermented to products other than lactic acid (ethanol, acetic acid, and formic acid), thereby lowering the product yield (mol lactic acid per mol carbohydrate) and rendering the product lactic acid more difficult to purify. Combet-Blanc et al in *Appl. Environm. Microbiol.*, 65: 4582-4585 (1999); *Appl. Environm. Microbiol.*, 61: 656-659 (1995); and *Internat. J. System. Bacteriol.*, 45: 9-16 (1995) disclose that the lactate yield on glucose is typically in the order of 88-92% (mol lactic acid per mol glucose). Furthermore, it was also disclosed that the enantiomeric purity of the (S)-lactic acid was 98%. *Bacillus coagulans* is homolactic, which means that the carbohydrate is fermented to lactic acid only. Furthermore DE 4000942 discloses that the enantiomeric purity of the lactic acid is close to 100%. *Bacillus coagulans* on the other hand ferments starch or liquefied starch or maltodextrines or maltooligosaccharides poorly. *Bacillus coagulans* and *Bacillus thermoamylovorans* have a relatively high pH optimum (6.0-7.0) for lactic acid production, which is substantially higher in pH units than the preferred application (working) pH range of glucoamylase (3.5-5). The application pH range of glucoamylase is thus not congruent with that of the microorganism. A lactic fermentation with the moderately thermophilic *Bacillus coagulans* and *Bacillus thermoamylovorans* operated as SSF at a pH that is optimal for the microorganism, reduces the activity of the glucoamylase. This can be compensated by adding more glucoamylase, but this will add to the costs. It is therefore a further object of the invention to provide a method for using the SSF system suitable for use of moderately thermophilic lactic acid producing microorganisms such as *Bacillus coagulans*. This strain has a high rate of substrate conversion and high production yield. It is known, that at high free glucose concentrations glucoamylase can give a reversed reaction to produce α-1,4, α-1,6 and α-1,3 linkages from glucose producing sugars, such as maltose, isomaltose and nigerose, which are poorly or not fermentable by moderately thermophilic lactic acid bacteria (e.g. Reilly (1985): Enzymic degradation of starch in: *Starch Conversion Technology* (van Beynum and Roels ed), Marcel Dekker Inc, New York, pp 101-142) Application of SSF with moderately thermophilic lactic acid bacteria prevents the accumulation of free glucose in fermentation broth thereby preventing or reducing the rate of reversion reactions and thereby preventing the accumulation of non-fermentable sugars such as isomaltose and nigerose. This increases the lactate yield on starch or liquefied starch and renders the lactic acid present in the fermentation broth less difficult to purify.

In a preferred embodiment the starch is saccharified, fermented, and optionally liquefied in a mixture of glucoamylase and at least one of pullulanase and α-amylase.

The instant process results in that substantially less residual sugars are obtained compared with conventional fermentation processes, making direct isolation of lactic acid possible. The present invention thus provides in an advantage of an easy and inexpensive work-up procedure, not longer necessitating a complex extraction step to separate the lactic acid from residual sugars. An additional advantage of the instant process is the possibility of using crude starch, since the low residual sugar amounts not longer require the use of purified starch as starting product. Usually residual sugar contents less than 5 g/l, preferably less than 2 g/l are easily obtainable with the process of the invention.

As indicated above, saccharification is performed by glucoamylase or a mixture of glucoamylase and α-amylase and/or pullulanase. Glucoamylase (EC 3.2.1.3, 1,4-α-D-glucan glucohydrolase) cleaves primarily α-1,4-glucosidic linkages at the non-reducing ends of both starch and the fragments left from α-amylase hydrolysis. Glucoamylase is an exohydrolase and attacks di-, oligo- and polysaccharides-containing glucose predominantly bound together by α-1,4-glucosidic linkages, though α-1,6-glucosidic linkages and α-1,3-glucosidic linkages are attacked at lower rates. This is of considerable industrial interest, as starch-hydrolysates after α-amylase treatment contain α-1,6-glucosidic linkages that must be cleaved if acceptable glucose yields are to be obtained. Since the activity of glucoamylase towards α-1,6-glucosidic linkages is low some commercially available glucoamylase preparations contain pullulanase. Pullulanase is a so-called debranching enzyme, which cleaves the α-1,6-glucosidic linkages present in starch and liquefied starch. To saccharify liquefied starch, enzyme-containing glucoamylase as main component as well as combination preparations containing glucoamylase and pullulanase appeared suitable for the process according to the present invention. The application pH range for glucoamylase and pullulanase was found to be optimal between 3.5 and 5. The application temperature range was found optimal between 55-70° C. The effect of calcium lactate and pH on the activity and stability of the enzyme was found not to become progressively worse as a result of the accumulation of fermentation product.

Even so, it is preferred to add the enzymes in at least two portions with regard to overall fermentation performance instead of a single addition at the beginning of the process. Commercially available glucoamylase/pullulanase preparations (ex Genencor and Novo Nordisk) were tested. All contained a considerable debranching activity. AMG™ E (ex Novo Nordisk), a glucoamylase with a high debranching activity, Dextrozyme™ E (containing glucoamylase and pullulanase) (ex NOVO Nordisk), and Optimax™ 7525 HP (containing glucoamylase and pullulanase) (ex Genencor) were also tested and again no large difference was observed between these preparations. Dextrozyme™ E performed slightly less than AMG™ E and Optimax™ 7525 HP regarding overall fermentation performance. AMG™ E and Optimax™ 7525 HP performed almost identical and both enzyme preparations were studied in detail (see Experimental).

The fermentation is performed by a moderately thermophilic lactic acid producing microorganism such as microorganisms derived from a strain of *Bacillus coagulans*, *Bacillus thermoamylovorans*, *Bacillus smithii*, *Geobacillus stearothermophilus*, or from mixtures thereof. These microorganisms are capable of growing at temperatures between 30-65° C. Thus these microorganism are better adjusted to work in the optimal working temperatures of the enzymes and the process according to the invention is usually conducted at a temperature between 30-70° C. The method of the invention is usually performed at pH 3-8.5, preferably at pH 5-6, more preferably at pH 5.35-5.80, most preferably at pH 5.50-5.60.

It is an advantage to adapt the thermophilic lactic acid-producing microorganism to the pH range as used in the process. The pH strongly influences the activity The enzymes become progressively more active at low pH values. However, the common pH ranges in which moderately thermophilic lactic acid-producing micro-organism perform optimal is between 6.0 and 7. Therefore, it is preferred to use moderately thermophilic lactic acid-producing microorganism, which has been adapted to have its maximum performance at low pH (between 5 and 6, preferably between 5.35-5.80, most preferably between 5.35-5.80). The technique of adapting the microorganism is known in the art. Adaptation or acclimation of moderately thermophilic lactic acid-producing bacteria to improve the performance at pH 5.35-5.8 was accomplished by carrying out 40-50 serial transfers in fermentation medium at pH 5.6.

The simultaneous saccharification and fermentation may be performed on a starch slurry or on any other starch-containing composition. Said starch may be liquefied or not. If a non-liquefied starch slurry or any other starch containing composition is used, the saccharification and fermentation may be combined with liquefaction and also an α-amylase may be present in the fermentation medium.

A full saccharification step may last up to 72 hours. However, it is possible to do a pre-saccharification of typically 40-90 minutes and then complete saccharification during fermentation. Said pre-saccharification step may be conducted at a temperature above 50° C., just prior to the fermentation. The most widely used process is a simultaneous saccharification and fermentation (SSF) process where there is no holding stage for the saccharification, meaning that fermenting organism and enzyme(s) is (are) added together. In the process according to the invention the moderately thermophilic lactic acid producing microorganism and enzyme(s) may also be added simultaneously. It goes without saying that the process according to the invention may also be performed by a pre-saccharification followed by a simultaneous saccharification and fermentation wherein an additional portion of the enzymes is added with the addition of the moderately thermophilic lactic acid-producing microorganism.

A starch slurry or slurry of a suitable starch-containing material or liquefied starch is fed into a fermenter. The microbial inoculum and nutrients are also fed into the fermenter. During the fermentation a suitable base such as calcium hydroxide, sodium hydroxide, potassium hydroxide, magnesium hydroxide, magnesium oxide, ammonia, ammonium hydroxide or a suitable carbonate such as calcium carbonate, sodium carbonate, sodium hydrogencarbonate, potassium carbonate, potassium hydrogencarbonate, magnesium carbonate, ammonium carbonate may be added for pH control.

When applied, in the liquefaction step of the invention, gelatinized starch or starch containing material is broken down (hydrolyzed) to maltodextrines with an average DE between 10 and 30. The term "gelatinization" means the process that transforms starch granules into starch paste. The hydrolysis may be carried out by acid treatment or enzymatically by α-amylase treatment. The α-amylase derived from a microorganism or a plant. Preferred α-amylases are of fungal or bacterial origin. A definition of α-amylase is given above.

The enzymatic liquefaction process may be carried out at a pH between 5 and 6, preferably between 5.35 and 5.80, and more preferably between 5.50 and 5.60. Thus, enzymatic liquefaction may advantageously be combined with either the pre-saccharification or the simultaneous saccharification and fermentation or with both. Acid hydrolysis, although its use is not wide spread, may also be used. The raw material may be milled (whole) cereals or rasped, shredded roots (potato, tapioca), tubers, whole grains, corns, cobs, wheat, barley, rye, milo, sugar-containing raw materials, such as molasses, fruit materials, sugar, cane or sugar beet, potatoes, cellulose-containing materials, such as wood or plant residues.

However, a side stream from starch processing such as co-called B-starch may also be used. Liquefaction is known in the art and needs no further elucidation here. As indicated-above, the liquefaction may also take place in combination with the saccharification and fermentation.

In a preferred embodiment of the invention the liquefaction step comprises the following steps:

1) the hot slurry is heated to between 60-95° C., preferably 80-85° C., and at least an α-amylase is added;
2) the slurry is jet-cooked at a temperature between 95-140° C., preferably 105-125° C. to complete gelanitization of the slurry;
3) the slurry is cooled to 60-95° C. and more α-amylase is added to finalize hydrolysis.

The liquefaction process may be carried out at pH 5-6, in particular at a pH between 5.35 and 5.80, most preferably at pH 5.50-5.60.

After combined saccharification and fermentation the formed lactic acid is optionally isolated from the fermentation medium and purified when necessary. Conventional purification/isolation methods for lactic acid are distillation, extraction, electrodialysis, adsorption, ion-exchange, crystallization and the like, and combinations of the above-mentioned purification/isolation methods. Distillation is the most commonly used technique. However, as explained above, with the process according to the invention the formation of non-fermentable sugars is reduced. Therefore, isolation or purification steps may be less complicated and sometimes even redundant. Further details on how to carry out distillation, and other techniques for recovering of lactic acid are well known to the skilled person. The invention is further illustrated by the following experiments, which are included without restricting the invention thereto.

EXAMPLES

SSF Experiments

Media and Culture Conditions

The culture *Bacillus coagulans* that was adapted to pH 5.65 was cultivated in a 3-liter glass jacketed stirred reactor equipped with temperature and pH control (Applikon, Schiedam, The Netherlands). The culture was routinely maintained, by transferring every 24 hours 180-200 ml of an actively fermenting culture to a fermenter containing a freshly prepared batch of maltodextrine-medium (see Table 1). Fermentations were performed with pure maltodextrines as well as liquefied starch from the Cargill Refinery in Blair (Nebraska, USA) and glucose syrup also from the Cargill Refinery in Blair (Nebraska, USA)(see Table 1).

TABLE 1

Composition of fermentation media for SSF and glucose fermentations

| Component | Liquefied starch medium | Maltodextrine medium | Glucose medium |
|---|---|---|---|
| Glucose syrup DE 98, 51.7% dry solids* | — | — | 800 g |
| Maltodextrine DE 11–14, 95% dry solids | — | 382 g | — |
| Liquefied starch DE 9–11, 35% dry solids* | 1.1 l | — | — |
| Diammonium phosphate | 7 g | 7 g | 7.0 g |
| Chalk (Whiting) | 26.7 g | 26.7 g | 26.7 g |
| Yeast extract (65% DS) | 3.4 g | 3.4 g | 3.4 g |
| Demineralised water (in l) | 0.5 l | 1.3 l | 1.0 l |
| AMG E ™ (Novozymes) first portion at start of fermentation | 0.65–0.7 ml | 0.65–0.7 ml | — |
| AMG E ™ (Novozymes) second portion after 24 hours fermentation | 0.3–0.35 ml | 0.3–0.35 ml | — |

*ex Cargill, Blair, Nebraska, USA

The temperature of the fermenters was controlled at 54-56° C. by means of a circulating water bath. The pH set point was a compromise between the optimum pH of the enzyme and the optimum for *Bacillus coagulans* that was adapted to pH 5.65. The fermentation was started at pH 6.0 and as a result of the formation of lactic acid allowed to drop. Upon reaching pH 5.55-5.75 the pH was controlled by the automatic addition of calcium hydroxide (250 g/l). After 24 hours fermentation the culture received a second portion of AMG E™ (Novozymes). The fermentation was allowed to proceed until the demand for calcium hydroxide ceased. This was the case after 30-40 hours incubation.

Results of SSF Experiments

The benchmark for the SSF fermentation was set by the fermentation with glucose syrup (DE 98) as substrate. The SSF study was started with a maltodextrine preparation from Roquette Freres (Glucidex™ 12, DE 11-14) and successfully finished. Two glucoamylase preparations were extensively tested: AMG E™ from Novozymes (glucoamylase with high debranching activity) and Optimax™ 7525 HP from Genencor (glucoamylase/pullulanase). A typical SSF fermentation on pure maltodextrines was free of residual sugars within 2 days. The main residual sugars present were glucose and isomaltose, however, at a consistently lower concentration than in comparable cultures that received DE 98 glucose syrup as substrate. Maltose concentrations were low (<50 mg/l) in contrast to comparable DE 98 cultures running at pH 6.4-6.6. A considerable amount of maltose was introduced in the fermentation with the addition of Glucidex 12. The fact that maltose could be fermented at low pH was a significant finding. The fermentation yield (mol (S)-lactate produced per mol glucose consumed) was slightly higher than 100%. Organic acids in sugar free SSF broth were analyzed and levels were comparable with *Bacillus coagulans* fermentations at pH 6.4-6.6. Below pH 5.55 the SSF fermentation was relatively slow. At pH 5.90 a 50% increase in total residual sugar was observed compared to cultures running between pH 5.55-5.75. Similar results were obtained using the crude liquefied starch. In the final stage, successful SSF experiments were performed with crude liquefied starch hydrolysates. There was no difference observed between the SSF fermentation on purified maltodextrines and the liquefied starch from the Cargill Refinery regarding fermentation time. Both SSF fermentations finished in 30-40 hours. Cultures containing crude liquefied starch or maltodextrin as substrate typically contained 180-200 g/l of (S)-lactic acid. The enantiomeric purity of the lactic acid was better than 99.5%.

SSF Experiments Using Various Moderately Thermophilic Microorganisms

SSF Experiments were Conducted with *Bacillus coagulans, Bacillus thermoamylovorans, Bacillus smithii, Geobacillus stearothermophilus*, and a mixture of all four. Hereto, the cultures were grown and used in the combined saccharification and fermentation of liquefied starch, using the same procedure and conditions as in the above-described SSF experiments. All microorganisms used (including the mixed culture), were able to produce lactic acid with high optical purity. The results are compiled in TABLE 2.

TABLE 2

SSF with various moderately thermophilic microorganisms

| Microorganism | Lactic acid yield (g/l) | Optical purity (% S-lactate) |
| --- | --- | --- |
| *Bacillus coagulans* | 35.5* | 99.8 |
| *Bacillus smithii* | 18.3* | 99.4 |
| *Bacillus thermoamylovorans* | 14.4** | 99.6 |
| *Geobacillus stearothermophilus* | 8.7** | 99.3 |
| Mixed culture of *Bacillus coagulans, Bacillus smithii, Bacillus thermoamylovorans* and *Geobacillus stearotrhermophilus* | 13.9** | 99.7 |

*4.5% starch input
**1.6% starch input

The invention claimed is:

1. A method for the production of lactic acid or a salt thereof wherein starch is subjected to a process of simultaneous saccharification and fermentation, the method comprising:
    saccharifying starch in a medium comprising at least a glucoamylase and simultaneously fermenting the starch using a microorganism; and
    optionally isolating lactic acid from the medium;
    wherein:
    the microorganism is at least one microorganism selected from the group consisting of moderately thermophilic *Bacillus* and moderately thermophilic *Geobacillus*, the microorganism being adapted to the pH range of 5-5.80.

2. The method according to claim 1 wherein the starch is saccharified, fermented, and optionally liquefied, in a mixture of glucoamylase and at least one of pullulanase and α-amylase.

3. The method according to claim 1 wherein lactic acid or of a salt thereof is made having an enantiomeric purity of at least 95%.

4. The method according to claim 1 wherein the process is performed at pH 3-8.5.

5. The method according to claim 4 wherein the process is performed at pH 5-6.

6. The method according to claim 4 wherein the thermophilic lactic acid-producing microorganism is adapted to the pH range as used in the process.

7. The method according to claim 1 wherein the process is performed at 30-70° C.

8. The method according to claim 1 wherein the glucoamylase is added in at least two portions.

9. The method according to claim 1 wherein the microorganism is derived from a strain of *Bacillus* coagulans, *Bacillus* thermoamylovorans, *Bacillus* smithii, *Geobacillus* stearothermophilus, or from a mixture thereof.

10. The method according to claim 5, wherein the process is performed at pH 5.35-5.80.

11. The method according to claim 6, wherein the process is performed at pH 5.50-5.60.

12. The method according to claim 2, wherein the mixture of glucoamylase with at least one of pullulanase and α-amylase is added in at least 2 portions.

* * * * *